US008048926B2

(12) United States Patent
Atlas

(10) Patent No.: US 8,048,926 B2
(45) Date of Patent: Nov. 1, 2011

(54) L-DOPA AMIDE DERIVATIVES AND USES THEREOF

(75) Inventor: Daphne Atlas, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 1305 days.

(21) Appl. No.: 11/196,739

(22) Filed: Aug. 4, 2005

(65) Prior Publication Data

US 2006/0025385 A1 Feb. 2, 2006

Related U.S. Application Data

(63) Continuation-in-part of application No. PCT/IL2004/000103, filed on Feb. 3, 2004.

(60) Provisional application No. 60/445,439, filed on Feb. 7, 2003.

(51) Int. Cl.
  A61K 31/131 (2006.01)
  C07C 211/03 (2006.01)
(52) U.S. Cl. ........................... 514/620; 564/306
(58) Field of Classification Search ............... 564/306
  See application file for complete search history.

(56) References Cited

U.S. PATENT DOCUMENTS

| | | | |
|---|---|---|---|
| 3,855,062 | A | 12/1974 | Renth et al. |
| 4,962,223 | A | 10/1990 | Cannata et al. |
| 5,073,547 | A | 12/1991 | Casagrande et al. |
| 5,354,885 | A | 10/1994 | Milman et al. |
| 5,607,969 | A | 3/1997 | Milman et al. |

FOREIGN PATENT DOCUMENTS

| | | |
|---|---|---|
| EP | 0231546 | 8/1987 |
| EP | 0351382 | 1/1990 |
| JP | 56115749 | * 9/1981 |
| WO | WO 03/089405 | 10/2003 |
| WO | WO 2004/069146 | 8/2004 |

OTHER PUBLICATIONS

Document No. 96:6432, retrieved from CAPLUS on May 16, 2008.*
RN 34996-80-0, retrieved from CAPLUS on May 16, 2008.*
RN 73148-96-6, retrieved from CAPLUS on May 16, 2008.*
RN 120346-34-1, retrieved from CAPLUS on May 16, 2008.*
Parkinsons disease, retrieved from the internet on May 21, 2008; URL: http://www.ninds.nih.gov/disorder/parkinsons_disease/parkinsons_disease.htm.*
Hughes, Bethan. Nature Reviews. 2008, 7, 791.*
Lamber, Didier. European Journal of Pharmaceutical Sciences. 2000, 11 Suppl. 2, S15-S27.*
Translation of JP 56115749A retrieved on Apr. 2010.*
Fingl et al. "General Principles", The Pharmacological Basis of Therapeutics, Ch.1(Sec.I): 1-46, 1975.
Wiczk et al. "Mechanism of Fluorescence Quenching of Tyrosine Derivatives by Amide Group", Chemical Physics Letters, 341: 99-106, 2001.
Wiczk et al. "Fluorescence Study of Neurohypophyseal Hormones and Their Analogues", European Biophysics Journal, 26: 183-193, 1997.
Aminoff "Parkinson's Disease and Other Extrapyramidal Disorders", Harrison's Principles of Internal Medicine, 14th Ed., Part 14(Chap.368): 2356-2359, 1998.
Gilgun-Sherki et al. "The CB1 Cannabinoid Receptor Agonist, HU-210, Reduces Levodopa-Induced Rotations in 6-Hydroxydopamine-Lesioned Rats", Pharmacology & Toxicology, 93: 66-70, 2003.
Hadjiconstantinou et al. "Aromatic L-amino Acid Decarboxylase Activity of Mouse Striatum Is Modulated Via Dopamine Receptors", Journal of Neurochemistry, 60: 2175-2180, 1993.
Bjorklund et al. "Cross-Species Neural Grafting in a Rat Model of Parkinson's Disease", Nature, 298: 652-654, 1982.
Badshah et al. "Catalytic Reduction of Azlactones in Alkaline Media. Synthesis of Amino Acids", The Journal of Organic Chemistry, 37: 2916-2918, 1972, Database Crossfire Beilstein, Beilstein Institut zur Foerderung der Chemischen Wissenschaften, Database Accession No. 4153771, 1988-2006. Abstract.
Beilstein "[2-(3,4-Dimethoxy-Phenyl)-1-Ethylcarbamoyl-Ethyl]-Carbamic Acid Tert-Butyl Ester", Database Crossfire Beilstein, Beilstein Institut zur Foerderung der Chemischen Wissenschaften, XP002422222, Database Accession No. 9346455, 2002. Abstract.
Beilstein "N-Benzoyl-β-(4-Hydroxy-3-Metoxyphenyl)-Alaninamide", Database Crossfire Beilstein, Beilstein Institut zur Foerderung der Chemischen Wissenschaften, XP002422225, Database Accession No. 2950518, 1988-2006. Abstract.
Galat "The Reaction of Phenylpyruvic Acid and Related Compounds With Ammonia", Journal of the American Chemical Society, 72: 4436-4439, 1950. p. 4438, col. 2.
Gouverneur et al. "Electrophilic Amination of 2-Azadienes", Tetrahedron, 52(21): 7585-7598, 1996, Database Crossfire Beilstein, Beilstein Institut zur Foerderung der Wisschenschaften, Database Accession No. 7539911. Abstract.
Ojima et al. "A New and Convenient Route to the Amides of Alpha-Amino Acids and Alpha-Hydroxy Acids by Means of the Palladium Catalyzed Facile Cleavage of 3-Substituted-4-Arylazetidin-2-Ones", Chemistry Letters, 7: 853-856, 1980. Table 1.
Rzepecki et al. ".Alpha., .Beta.-Dehydro-3,4-Dihydroxyphenylalanine Derivatives: Potential Schlerotization Intermediates in Natural Composite Materials", Archives of Biochemistry and Biophysics, 285(1): 17-26, 1991, Database CA [Online], Chemical Abstracts Service, Database Accession No. 1991:159298 CAPLUS, 1991.
Wiczk et al. "Mechanism of Fluorescence Quenching of Tyrosine Derivatives by Amide Group", Chemical Physics Letters, 341(1-2): 99-106, 2001. Database Crossfire Beilstein, Beilstein Institut zur Foerderung der Chemischen Wissenschaften, Database Accession No. 892 3284, 2001. Abstract. International Preliminary Report on Patentability Dated Sep. 28, 2006 From the International Bureau of WIPO Re.: Application No. PCT/IL2004/000103.
Official Action Dated May 28, 2008 From the US Patent and Trademark Office Re.: U.S. Appl. No. 11/196,739.
Communication Pursuant to Article 94(3) EPC Dated Jan. 22, 2009 From the European Patent Office Re.: Application No. 04707616.1.
International Search Report Dated Aug. 7, 2006 From the International Searching Authority Re.: Application No. PCT/IL2004/000103.

(Continued)

Primary Examiner — Shawquia E Young

(57) ABSTRACT

L-DOPA amide derivatives, pharmaceutical compositions containing same and their use in the treatment of conditions associated with impaired dopaminergic activity/signaling (e.g., Parkinson disease) are disclosed.

17 Claims, 4 Drawing Sheets

OTHER PUBLICATIONS

Office Action Dated Sep. 29, 2009 From the Israeli Patent Office Re.: 170096 and Its Translation Into English.
Official Action Dated Jan. 10, 2008 From the US Patent and Trademark Office Re.: U.S. Appl. No. 11/196,739.
Supplementary Partial European Search Report Dated Mar. 7, 2007 From the European Patent Office Re.: Application No. 04707616.1.
Written Opinion Dated Aug. 7, 2006 From the International Searching Authority Re.: Application No. PCT/IL2004/000103.
Beilstein "[1-Carbomoyl-2-(3,4-Dimethoxy-Phenyl)-Ethyl]-Carbamic Acid TertButyl Ester", Database Crossfire Beilstein, Beilstein Institut zur Foerderung der Chemischen Wissenschaften, Database Accession No. 8923284, XP002422223, 2001.
Beilstein "N-Benzoyl-?-(4-Hydroxy-3-Metoxyphenyl)-Alaninamide", Database Crossfire Beilstein, Beilstein Institut zur Foerderung der Chemischen Wissenschaften, XP002422225, Database Accession No. 2950518, 1988-2006. Abstract.
Rzepecki et al. "α,β-Dehydro-3,4-Dihydroxyphenylalanine Derivatives: Potential Schlerotization Intermediates in Natural Composite Materials", Archives of Biochemistry and Biophysics, XP24762045, 285(1): 17-26, Feb. 15, 1991. Database CA [Online], Chemical Abstracts Service, Database Accession No. 1991:159298 CAPLUS, 1991.

* cited by examiner

L-DOPA AMIDE DERIVATIVES AND USES THEREOF

RELATED APPLICATIONS

This application is a Continuation-In-Part (CIP) of PCT Application No. PCT/IL2004/000103, filed on Feb. 3, 2004, which claims priority from U.S. Provisional Patent Application No. 60/445,439, filed on Feb. 7, 2003.

FIELD AND BACKGROUND OF THE INVENTION

The present invention relates to novel compounds for the treatment of Parkinson disease and other conditions associated with impaired dopaminergic signaling in the brain, and, more particularly, to L-DOPA derivatives, which can serve as efficient L-DOPA prodrugs for treating such conditions.

Parkinson's disease (PD) is a common neurological syndrome characterized by the selective loss of dopaminergic neurons in the nigrostriatal tract, a selective site in the brain. Specifically, dopamine neurons in the substantia nigra degenerate, resulting in the loss of dopamine (3,4-dihydroxyphenethylamine) input to the striatum. In addition to the loss of dopaminergic neurons, other regions in the brain are affected, impairing vital activities. Altogether, the reduction of dopamine in the striatum and the impaired activity in other brain regions cause sever clinical symptoms such as increased muscle rigidity, resting tremor, bradykinesia, abnormalities of posture and gait, slowness of voluntary movement and slurred speech. The level of decrease in dopamine synthesis correlates with the severity of the symptoms. Without treatment, PD patients eventually progress to a tragically debilitating rigid state.

Current treatment regimes for PD consist primarily of pharmacological supplementation of the dopaminergic loss, preferably with dopamine agonists and levodopa (also known as 3-hydroxy-L-tyrosine, 3,4-dihydroxy-L-phenylalanine and L-DOPA). L-DOPA is the metabolic precursor of dopamine, which, unlike dopamine, can readily cross the blood-brain barrier. Administration of L-DOPA therefore results in increased levels thereof in the brain, where it is converted to dopamine by the enzyme Aromatic L-Amino Acid Decarboxylase (AADC). L-DOPA thus plays a major role in replenishing the loss of dopamine and is typically administered in combination with a DOPA decarboxylase inhibitor that inhibits decarboxylation of L-DOPA in the periphery (for a general review of PD treatments currently in use see Adams et al., Principles of Neurology 4th Ed. McGraw Hill, New York 1989).

However, conventional treatments for Parkinson's disease with L-DOPA have proven to be inadequate for many reasons of record in the medical literature. The systemic administration of levodopa, although producing clinically beneficial effects at first, is complicated by the need to reduce dosages that were well tolerated at the outset in order to avoid adverse side effects. Some patients also become less responsive to levodopa, so that previously effective doses eventually fail to produce any therapeutic benefit. For such reasons, the benefits of levodopa treatment often begin to diminish after about 3 or 4 years of therapy irrespective of the initial therapeutic response.

In addition, the augmentation of systemic levels of levodopa, necessary to establish therapeutically effective levels at the site of interest, i.e., the brain, have been reported to cause several gastrointestinal adverse effects (including anorexia, nausea and vomiting due to the stimulation of an emetic center located in the brain stem outside the blood-brain barrier), cardiovascular effects (mostly due to the increased catecholamine formation peripherally), dyskinesia, and drastic behavioral effects (depression, anxiety, agitation, insomnia, somnolence, confusion, delusions, hallucinations, psychotic episodes and other changes in mood or personality).

The peripheral administration of levodopa is further complicated by the fact that only about 1-3% of administered levodopa actually enters the brain unaltered, the remainder being metabolized extracerebrally, predominantly by decarboxylation to dopamine, which does not penetrate the blood-brain barrier. This means that levodopa must be given in large amounts when it is used alone. The co-administration of a peripheral dopadecarboxylase has been found to reduce the dosage requirements and some of the side effects, although only marginally.

Finally, certain fluctuations in clinical response to levodopa occur with increasing frequency as treatment continues. In some patients, these fluctuations relate to the timing of levodopa intake, and they are then referred to as wearing-off reactions or end-of-dose akinesia. In other instances, fluctuations in clinical state are unrelated to the timing of doses (on-off phenomenon). In the on-off phenomenon, off-periods of marked akinesia alternate over the course of a few hours with on-periods of improved mobility but often marked dyskinesia. (Aminoff, "Parkinson's Disease and other Extrapyramidal Disorders", in Harrison's Principles of Internal Medicine, 14th Ed. McGraw-Hill, (1998), pp. 2356-2359), and Katzung Basic & Clinical Pharmacology, 6th Ed., Appleton & Lange, Norwalk, Conn.).

It is well accepted in the art that many of the problems recited above result form the unfavorable pharmacokinetic properties of L-DOPA, and, more particularly, from its poor water solubility, bioavailability and fast degradation in vivo.

It was therefore suggested that the use of an L-DOPA derivative, which can release L-DOPA in vivo and is characterized by improved pharmacokinetic properties, might overcome the above limitations. Thus, U.S. Pat. Nos. 5,354,885 and 5,607,969 disclose a preparation and use of L-DOPA ethyl ester for the treatment of PD. Such an L-DOPA derivative is highly water-soluble and was thought to have pharmacokinetic properties that are highly favorable as compared with those of L-DOPA. However, it was found that this L-DOPA derivative undergoes a fast hydrolysis to L-DOPA before it reaches the brain, which downgrades its consistency and efficiency as a PD treatment.

As is well recognized in the art, and is further detailed hereinbelow, amides are typically stable compounds that undergo slower hydrolysis than their corresponding esters. Several L-DOPA amide derivatives are disclosed in Wiczk et al. (Chemical Physics Letters 341 (2001) 99-106). However, while Wiczk et al. have prepared these amide derivatives in order to evaluate the fluorescence quenching of tyrosine derivatives by amide group, and thus the use of fluorescent aromatic amino acids as internal probes in conformational analysis, the use of such derivatives in the treatment of Parkinson disease and related conditions have not been explored.

There is thus a widely recognized need for, and it would be highly advantageous to have, L-DOPA derivatives for the treatment of Parkinson disease and related conditions, devoid of the above limitations.

SUMMARY OF THE INVENTION

According to the present invention there are provided novel and improved L-DOPA prodrugs for use in the treatment of Parkinson disease and related conditions.

The L-DOPA prodrugs of the present invention are compounds having a general formula:

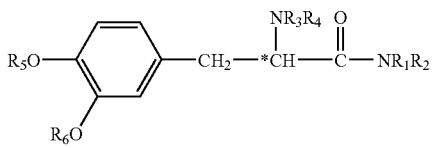

wherein:

*C denotes a chiral carbon;

$R_1$, $R_2$, $R_3$ and $R_4$ are each independently selected from the group consisting of hydrogen, alkyl having 1-30 carbon atoms, alkenyl having 1-30 carbon atoms, alkynyl having 1-30 carbon atoms, cycloalkyl, aryl, O-carboxy, C-carboxy, carbonyl, thiocarbonyl, O-carbamyl, O-thiocarbamyl and a fatty acid acyl, or, alternatively, $R_1$ and $R_2$ and/or $R_3$ and $R_4$ form a five- or six-membered ring; and $R_5$ and $R_6$ are each independently selected from the group consisting of hydrogen, alkyl, cycloalkyl, aryl and phosphonyl, or a pharmaceutically acceptable salt thereof.

As is detailed hereinbelow, these compounds are characterized by high permeability through the blood brain barrier.

Being L-DOPA derivatives, the *C chiral carbon in the compounds of the present embodiments preferably has an S-configuration.

Preferred compounds for use as L-DOPA prodrugs according to the present embodiments include compounds wherein $R_5$ and $R_6$ are each hydrogen.

Additional preferred compounds for use as L-DOPA prodrugs according to the present embodiments include compounds wherein $R_1$ and $R_2$ are each hydrogen.

Additional preferred compounds for use as L-DOPA prodrugs according to the present embodiments include compounds wherein $R_3$ and $R_4$ are each hydrogen.

More preferred compounds according to the present embodiments include compounds wherein at least one of $R_1$, $R_2$, $R_3$ and $R_4$, preferably $R_3$ and/or $R_4$ is carbonyl, e.g., acetyl.

Additional preferred compounds according to the present embodiments include compounds wherein at least one of $R_1$, $R_2$, $R_3$ and $R_4$ is an alkyl, alkenyl or alkynyl having 1-30 carbon atoms, or, alternatively, at least one of $R_1$, $R_2$, $R_3$ and $R_4$ is a fatty acid acyl, derived from, for example, myristic acid, lauric acid, palmitic acid, stearic acid, oleic acid, arachidonic acid, linoleic acid or linolenic acid.

Representative examples of L-DOPA prodrugs according to the present embodiments include α-amino-3,4-dihydroxybenzenepropanamide, α-N-acetyl-3,4-dihydroxy-benzenepropanamide and pharmaceutically acceptable salts thereof.

According to another aspect of the present invention there is provided a pharmaceutical composition for use in the treatment of a condition associated with impaired dopaminergic signaling, comprising, as an active ingredient, any of the compounds described hereinabove and a pharmaceutically acceptable carrier.

The condition can be, for example, Parkinson disease, Tourette's syndrome, attention deficit hyperactive disorder, generation of pituitary tumors or schizophrenia.

In a preferred embodiment, the pharmaceutical composition is packaged in a packaging material and identified in print, in or on the packaging material, for use in the treatment of such a condition.

In a preferred embodiment, the pharmaceutical composition further comprises at least one antioxidant, such as, but not limited to ascorbic acid, sodium metabisulfate, lipoic acid, N-acetyl cysteine, CB4, CB3, AD4, AD6, AD7 and Vitamin E.

In another preferred embodiment, the pharmaceutical composition further comprises at least one decarboxylase inhibitor (e.g., an L-DOPA decarboxylase inhibitor or a monoamine oxidase-B inhibitor).

According to further features in the preferred embodiments of the invention described below, the pharmaceutically acceptable carrier is a solution, either aqueous or non-aqueous.

According to still further features in the described preferred embodiments the aqueous solution is a buffered acidic solution, whereby the compound is in a form of a free base.

According to still further features in the described preferred embodiments the pharmaceutically acceptable carrier is a solid carrier.

According to still further features in the described preferred embodiments the pharmaceutical composition of the present invention can be formulated for administration by a route selected from the group consisting of buccal, oral, sublingual, parenteral, intranasal, intramuscular, intraventricular, subcutaneous, intraduodenal and rectal route.

According to yet another aspect of the present invention there is provided a method of treating a condition associated with impaired dopaminergic signaling, as described hereinabove, which comprises administering to a subject in need thereof a therapeutically effective amount of the pharmaceutical composition described above.

The administering can be effected buccally, orally, sublingually, parenterally, intranasally, intramuscularly, intraventricularly, subcutaneously, intraduodenally or rectally.

According to still another aspect of the present invention there is provided a use of any of the compounds described herein for the manufacture of a medicament identified for the treatment of a condition associated with impaired dopaminergic signaling.

According to an additional aspect of the present invention there is provided a process of preparing an L-DOPA prodrug as described hereinabove, which comprises:

(a) providing a compound having the general Formula II:

Formula II

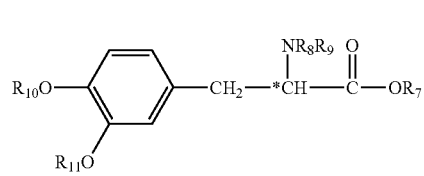

wherein: *C denotes a chiral carbon; $R_7$ is hydrogen or alkyl; $R_8$ and $R_9$ are each independently selected from the group consisting of hydrogen, alkyl having 1-30 carbon atoms, alkenyl having 1-30 carbon atoms, alkynyl having 1-30 carbon atoms, cycloalkyl, halo, aryl, O-carboxy, C-carboxy, carbonyl, thiocarbonyl, O-carbamyl, O-thiocarbamyl, and a fatty acid acyl, or, alternatively, $R_8$ and $R_9$ form a five- or six-membered ring; and $R_{10}$ and $R_{11}$ are each independently selected from the group consisting of hydrogen, alkyl, cycloalkyl, aryl and phosphonyl, (b) reacting the compound having the general Formula II, with an aqueous ammonia solution, thereby producing the compound having the general Formula I, wherein $R_1$ and $R_2$ are each hydrogen; and (c) optionally, reacting the compound obtained in (b) with a reactive derivative of the alkyl having 1-30 carbon atoms, alkenyl having 1-30 carbon atoms, alkynyl having 1-30 carbon atoms, cycloalkyl, halo, aryl, O-carboxy, C-carboxy, carbonyl, thiocarbonyl, O-carbamyl, O-thiocarbamyl, or the fatty acid, thereby obtaining the compound having the general Formula I, wherein $R_1$ and $R_2$ are each independently selected from the group consisting of alkyl having 1-30 carbon atoms, alkenyl having 1-30 carbon atoms, alkynyl having 1-30 carbon atoms, cycloalkyl, halo, aryl, O-carboxy, C-carboxy, carbonyl, thiocarbonyl, O-carbamyl, O-thiocarbamyl, or fatty acid acyl, or, alternatively, $R_1$ and $R_2$ form a five- or six-membered ring, as is detailed hereinbelow.

According to further features in preferred embodiments of the invention described below, the process further comprises purifying the compound, preferably by recrystallization and column chromatography. The resulting compound preferably has a purity of at least 90%.

According to still further features in the described preferred embodiments the re-crystallization is performed in the presence of at least one antioxidant.

The present invention successfully addresses the shortcomings of the presently known configurations by providing novel L-DOPA derivatives with improved pharmacokinetic properties.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
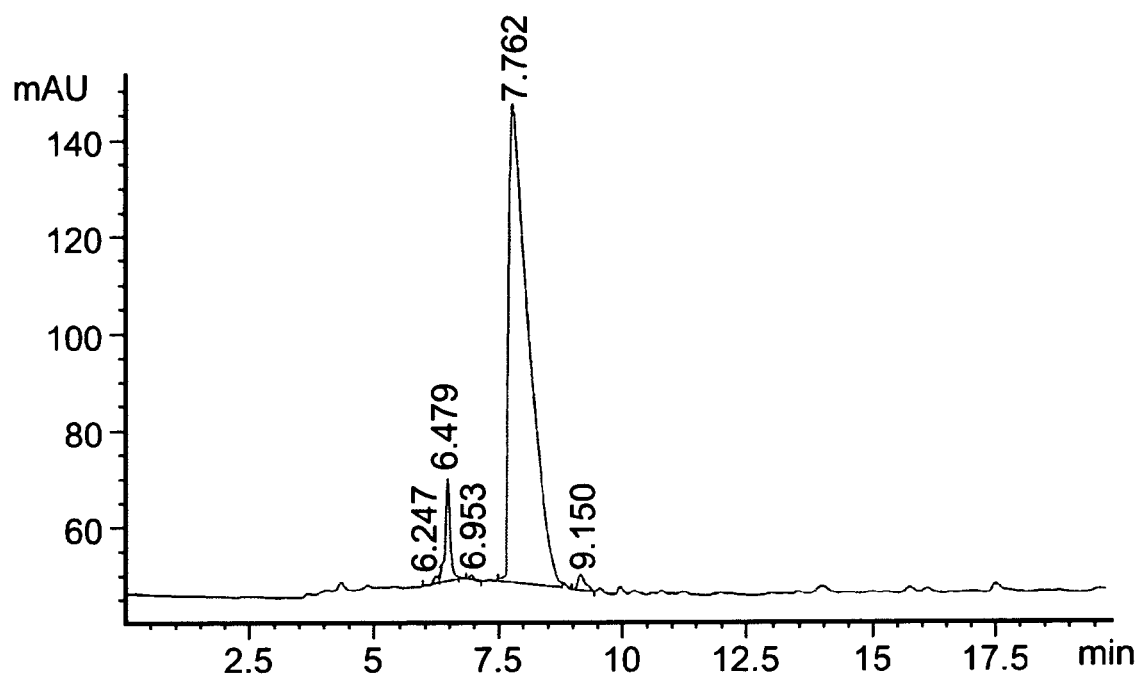
FIG. 1 presents a HPLC chromatogram of a representative example of a L-DOPA amide derivative (L-Dopamide) according to the present embodiments.

The present invention is of L-DOPA amide derivatives which can be used in the treatment of conditions associated with impaired dopaminergic signaling (e.g., Parkinson disease). Specifically, the present invention is of L-DOPA amide derivatives, which can release in the brain, selectively and effectively, L-DOPA and can therefore be used as novel L-DOPA prodrugs. The present invention is further of pharmaceutical compositions containing L-DOPA amide derivatives, of uses thereof in the treatment of Parkinson disease and related conditions and of processes of preparing the L-DOPA amide derivatives.

The principles and operation of the compounds, pharmaceutical compositions, methods, uses and processes according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As is discusses hereinabove, the most common prevalent treatment of Parkinson disease, which includes co-administration of L-DOPA and an L-DOPA decarboxylase inhibitor, suffers many disadvantages, with poor pharmacokinetics properties being one of the major limitations thereof.

L-DOPA is a metabolic precursor, or a prodrug, of dopamine, which upon administration, penetrates the blood brain barrier (BBB) and undergoes an enzymatic decarboxylation in the brain, to thereby release dopamine. However, due to fast and non-specific decarboxylation, which thus mainly occurs in the periphery, fast excretion and relatively low BBB permeability, high doses of L-DOPA are required in order to achieve a substantial accumulation thereof in the brain, and as a result substantial amelioration in PD patients. Such a high dosage regime is typically associated with sever adverse side effects and is further limited by diminished response after a few years.

In a search for new and improved treatment for PD and related diseases and disorders, it was envisioned, at first, that ester derivatives of L-DOPA would serve as potent prodrugs for treating PD. However, as esters undergo fast enzymatic hydrolysis in vivo, such prodrugs were also found to be disadvantageous, similar to L-DOPA.

While conceiving the present invention, the present inventor has hypothesized that L-DOPA amide derivatives could serve as highly potent L-DOPA prodrugs, devoid of the limitations associated with the L-DOPA and its derivatives described above. The underlying basis of this hypothesis was as follows:

Amides are neutral compounds at physiological pH. Hence, as opposed to L-DOPA, which has a zwitterionic form, the carboxylic group in a corresponding amide is neutralized, thus rendering such compounds less hydrophilic and thereby more membrane permeable. Being more permeable, the penetration of amides through the BBB is facilitated, providing for enhanced accumulation thereof in the brain.

In addition, amides are hydrolysed in vivo by amido peptidase. As is well known in the art, the rate of enzymatic hydrolysis is determined by the nature of the hydrolysed bond. Amides are known as much more stable molecules than esters and acids, and therefore the hydrolysis rate of amides by amidopeptidases is significantly reduced as compared with the corresponding acid and ester peptidases. Hence, it is expected that the rate of hydrolysis of an amide derivative of L-DOPA in the periphery would be substantially reduced, providing for enhanced accumulation thereof in the brain.

The same feature applies also for brain derived, endogenous amidopeptidases, such that once the L-DOPA amide derivative penetrates the BBB, the rate of its conversion into L-DOPA is relatively slow. This feature may result in the gradual formation of L-DOPA, thus mimicking a slow release effect of the drug.

The slow hydrolyses of amides together with its enhanced BBB permeability, enables the administration of lower doses of L-DOPA amide derivatives, thus providing for reduced adverse side effects and prolonged treatment period.

Moreover, as amides do not function as substrates of the endogenous aromatic amino acid decarboxylase (AADC), the prevalent required co-administration of an AADC inhibitor can be avoided. Omitting, or reducing, the amount of such an inhibitor in PD therapy is highly advantageous since it may also reduce the side effects associated with the present PD treatment. As is well known in the art, daily administration of therapeutic agents, as in chronic patients such as PD patients, typically results in accumulation of toxic levels of the drug. Hence, omitting any component from a treatment system is preferable. Furthermore, several reports have associated the diminished efficacy of the present L-DOPA treatment with the co-administration of an AADC inhibitor. Omitting, or reducing, the amount of this inhibitor can therefore further provide for prolonged treatment.

While reducing the present invention to practice, representative examples of L-DOPA amide derivatives have been successfully synthesized. As is demonstrated in the Examples section that follows, these derivatives were found highly efficient in increasing the dopamine level in an acceptable animal model and were further found beneficial with respect to their inactivity as substrates of DOPA decarboxylase.

Thus, according to one aspect of the present invention, there are provided L-DOPA amide derivatives, which are characterized by pharmacokinetic properties that are superior to the presently known L-DOPA derivatives, as outlined hereinabove, and can therefore be beneficially used in the treatment of PD and related conditions associated with impaired dopaminergic signaling.

Each of the L-DOPA amide derivatives of the present invention has the following general formula:

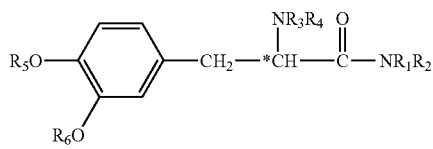

wherein:
*C denotes a chiral carbon;
$R_1$, $R_2$, $R_3$ and $R_4$ are each independently selected from the group consisting of hydrogen, alkyl having 1-30 carbon atoms, alkenyl having 1-30 carbon atoms, alkynyl having 1-30 carbon atoms, cycloalkyl, aryl, O-carboxy, C-carboxy, carbonyl, thiocarbonyl, O-carbamyl, O-thiocarbamyl, and a fatty acid acyl, or, alternatively, $R_1$ and $R_2$ and/or $R_3$ and $R_4$ form a five- or six-membered ring; and
$R_5$ and $R_6$ are each independently selected from the group consisting of hydrogen, alkyl, cycloalkyl, aryl and phosphonyl, or a pharmaceutically acceptable salt thereof.

As used herein, the term "alkyl" refers to a saturated aliphatic hydrocarbon including straight chain and branched chain groups. The alkyl group preferably has between 1 and 30 carbon atoms, more preferably between 1 and 20 carbon atoms. While lower alkyls, e.g., of between 1 and 6 carbon atoms may facilitate the formulation of the compounds, higher alkyls provides for enhanced permeability thereof through the BBB.

The alkyl group, according to the present invention, may be substituted or non-substituted. When substituted, the substituent group can be, for example, cycloalkyl, alkenyl, aryl, heteroaryl, heteroalicyclic, hydroxy, alkoxy, aryloxy, thiohydroxy, thioalkoxy, thioaryloxy, halo, carboxy, alkoxycarbonyl, thiocarboxy, carbamyl, and amino, as these terms are defined herein.

As used herein, the term "cycloalkyl" refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. The cycloalkyl group, according to the present invention, may be substituted or non-substituted. When substituted, the substituent group can be, for example, alkyl, cycloalkyl, alkenyl, aryl, heteroaryl, heteroalicyclic, hydroxy, alkoxy, aryloxy, thiohydroxy, thioalkoxy, thioaryloxy, halo, carboxy, alkoxycarbonyl, thiocarboxy, carbamyl, and amino, as these terms are defined herein.

The term "alkenyl" refers to an alkyl group which consists of at least two carbon atoms and at least one carbon-carbon double bond.

The term "alkynyl" refers to an alkyl group which consists of at least two carbon atoms and at least one carbon-carbon triple bond.

As is discussed above, both the alkenyl and the alkynyl groups preferably have between 1 and 30 carbon atoms.

An "aryl" group refers to an all-carbon monocyclic or fused-ring polycyclic (i.e., rings which share adjacent pairs of carbon atoms) group having a completely conjugated pi-electron system. Examples, without limitation, of aryl groups are phenyl, naphthalenyl and anthracenyl. The aryl group, according to the present invention, may be substituted or non-substituted. When substituted, the substituent group can be, for example, alkyl, cycloalkyl, alkenyl, aryl, heteroaryl, heteroalicyclic, hydroxy, alkoxy, aryloxy, thiohydroxy, thioalkoxy, thioaryloxy, halo, carboxy, alkoxycarbonyl, thiocarboxy, carbamyl, and amino, as these terms are defined herein.

The term "C-carboxy" refers to a —C(=O)—OR' group, where R' is hydrogen, alkyl, cycloalkyl, alkenyl, aryl, heteroaryl (bonded through a ring carbon) or heteroalicyclic (bonded through a ring carbon) as defined herein.

The term "O-carboxy" refers to a R'—C(=O)—O— group, where R' is hydrogen, alkyl, cycloalkyl, alkenyl, aryl, heteroaryl (bonded through a ring carbon) or heteroalicyclic (bonded through a ring carbon) as defined herein.

The term "carbonyl" refers to a —C(=O)—R' group, where R' is as defined hereinabove.

The term "thiocarbonyl" refers to a —C(=S)—R' group, where R' is as defined hereinabove.

An "O-carbamyl" group refers to an —OC(=O)—NR'R" group, where R' is as defined hereinabove and R" is as defined for R'.

An "O-thiocarbamyl" group refers to an —OC(=S)—NR'R" group, where R' is and R" are as defined hereinabove.

A "fatty acid acyl" refers to a R'''C(=O)—O— group, where R''' is a saturated or unsaturated hydrocarbon chain having at least 10 carbon atoms.

The term "alkoxy" refers to both an —O-alkyl and an —O-cycloalkyl group, as defined hereinabove. Representative examples of alkoxy groups include methoxy, ethoxy, propoxy and tert-butoxy.

The —O-alkyl and the O-cycloalkyl groups, according to the present invention, may be substituted or non-substituted. When substituted, the substituent group can be, for example, cycloalkyl, alkenyl, aryl, heteroaryl, heteroalicyclic, hydroxy, alkoxy, aryloxy, thiohydroxy, thioalkoxy, thioaryloxy, halo, carboxy, alkoxycarbonyl, thiocarboxy, carbamyl, and amino, as these terms are defined herein.

The term "thioalkoxy" refers to both an —S-alkyl group, and an —S-cycloalkyl group, as defined herein.

The term "hydroxy" refers to an —OH group.

The term "thiohydroxy" refers to an —SH group.

An "aryloxy" group refers to both an —O-aryl and an —O-heteroaryl group, as defined herein.

A "thioaryloxy" group refers to both an —S-aryl and an —S-heteroaryl group, as defined herein.

The term "amino" refers to a —NR'R" group, with R' and R" as defined hereinabove.

The term "alkoxycarbonyl", which is also referred to herein interchangeably as "carbalkoxy", refers to a carboxy group, as defined hereinabove, where R' is not hydrogen.

The term "heteroaryl" group includes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system.

The term "halo" refers to a fluorine, chlorine, bromine or iodine atom.

The term "phosphonyl" describes an —P(=O)(OR')$_2$ group, with R' as defined hereinabove.

Being derived from L-DOPA, the compounds of the present invention preferably have the same configuration, namely, the chiral carbon (denoted as *C in Formula I) has an S configuration.

In a preferred embodiment of the present invention, $R_5$ and $R_6$ in Formula I hereinabove are each hydrogen, as in the corresponding L-DOPA, such that the phenyl ring is substituted at positions 3 and 4 thereof by two hydroxy group. However, modification of at least one of these hydroxy groups, as is described, for example, in U.S. Pat. No. 5,073, 547, can further enhance the bioavailability of the compound. Hence, the phenyl ring in Formula I can alternatively be substituted at positions 3 and 4 thereof by one or more alkoxy, cycloalkoxy or aryloxy groups, as these terms are defined hereinabove and/or be phosphorylated by a phosphonyl group, as defined hereinabove.

As is discussed hereinabove, the presence of an amide moiety within the compounds of the present invention provides for its advantageous use for treating impaired dopaminergic signaling, as in the case of PD.

The amide group in the compounds of the present invention can be derived from the carboxylic group of L-DOPA, (C(=O)NR$_1$R$_2$) in the Formula above and/or from the amine group of L-DOPA (NR$_3$R$_4$ in the formula above, such that R$_3$ or R$_4$ is a carbonyl group.

Hence, in a preferred embodiment, R$_3$ and R$_4$ are each hydrogen, such that the amide group is derived from the carboxylic group of L-DOPA. Although some compounds within this embodiment of the present invention are known (see, Wiczk et al. supra), such compounds have never been therapeutically used, as is described herein.

In another preferred embodiment, at least one of R$_1$, R$_2$, R$_3$ and R$_4$ is a carbonyl group, as defined hereinabove. Preferably, R$_3$ and/or R$_4$ are a carbonyl group, such that at least two amide bonds, one derived from the carboxylic group and one from the amine group, are present in the compound. Such compounds are highly advantageous since they are completely neutralized and very slowly hydrolyzed (due to the presence of two amide moieties). As is discussed in detail hereinabove, these features provide for high in vivo stability and brain permeability and thus for high accumulation of the compounds in the brain, reducing the need for high dosage.

In order to further enhance the brain membrane permeability of the compounds of the present invention, hydrophobic moieties are preferably attached thereto. Thus, in another preferred embodiment, at least one of R$_1$, R$_2$, R$_3$ and R$_4$ is an alkyl, alkenyl or alkynyl having 1-30 carbon atoms, preferably between 10 and 30 carbon atoms.

Such a hydrophobic moiety can alternatively be derived from a fatty acid, such that in yet another preferred embodiment, at least one of R$_1$, R$_2$, R$_3$ and R$_4$ is a fatty acid acyl, as this phrase is defined hereinabove.

Representative examples of fatty acids from which such as acyl can be derived from include, without limitation, myristic acid, lauric acid, palmitic acid, stearic acid, oleic acid, arachidonic acid, linoleic acid and linolenic acid.

As is exemplified in the Examples section that follows, two representative examples of the L-DOPA amide derivatives of the present invention have been successfully synthesized, purified and characterized: α-amino-3,4-dihydroxy-benzenepropanamide (also referred to herein as 2-amino-3-(3,4-dihydroxyphenyl)propaneamide) and, the more advantageous α-N-acetyl-3,4-dihydroxy-benzenepropanamide (also referred to herein as 2-N-acetyl-3-(3,4-dihydroxyphenyl) propaneamide).

Hence, according to another aspect of the present invention there is provided a process of preparing the compounds of the present invention described hereinabove. The process is effected by providing a compound having the general formula:

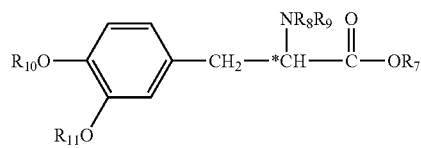

wherein:
  *C denotes a chiral carbon;
  R$_7$ is hydrogen or alkyl;
  R$_8$ and R$_9$ are each independently selected from the group consisting of hydrogen, alkyl having 1-30 carbon atoms, alkenyl having 1-30 carbon atoms, alkynyl having 1-30 carbon atoms, cycloalkyl, halo, aryl, O-carboxy, C-carboxy, carbonyl, thiocarbonyl, O-carbamyl, O-thiocarbamyl, and a fatty acid acyl, or, alternatively, R$_8$ and R$_9$ form a five- or six-membered ring;

$R_{10}$ and $R_{11}$ are each independently selected from the group consisting of hydrogen, alkyl, cycloalkyl, aryl and phosphonyl; and reacting the compound with an aqueous ammonia solution, to thereby produce a compound according to the present invention wherein $R_1$ and $R_2$ are each hydrogen.

The resulting compound can optionally be further reacted with a reactive derivative of an alkyl having 1-30 carbon atoms, alkenyl having 1-30 carbon atoms, alkynyl having 1-30 carbon atoms, cycloalkyl, halo, aryl, O-carboxy, C-carboxy, carbonyl, thiocarbonyl, O-carbamyl, O-thiocarbamyl or fatty acid, to thereby produce a compound according to the present invention wherein $R_1$ and/or $R_2$ are not hydrogen.

As used herein the phrase "reactive derivative" refers to a derivative of a substance, which includes a reactive group that can be easily reacted with another group so as to produce a new compound that comprises a new functional group. Representative examples of a reactive group include halogen (halo), amino, hydroxy and alkoxy. Representative examples of a reactive derivative according to the present invention therefore include, without limitation, alkyl chloride, a metal salt of an alkoxy, acyl chloride, ester and carboxylic anhydride.

In cases where *C has an S configuration and $R_7$, $R_8$, $R_9$, $R_{10}$ and $R_{11}$ are each hydrogen, the starting material of the process is L-DOPA.

In cases where *C has an S configuration, $R_7$ is alkyl and $R_8$, $R_9$, $R_{10}$ and $R_{11}$ are each hydrogen, the starting material of the process is an L-DOPA alkyl ester. The process is therefore effected by providing L-DOPA and reacting it with the appropriate alcohol (represented by $R_7OH$). Such an esterification can be performed using methods known in the art (see, for example, U.S. Pat. No. 5,354,885).

Any derivative of the starting materials described above can be reacted with ammonia, to produce a non-substituted amide derivative of the compound of the invention described above. The resulting amine can be further reacted with a reactive derivative as described above, to produce a substituted amide derivative.

Hence, in one exemplary particular, L-DOPA is converted to an ester thereof (e.g., a methyl ester), and is thereafter reacted with an aqueous solution of ammonia, to thereby produce L-Dopamide (2-amino-3-(3,4-dihydroxyphenyl) propaneamide).

In another exemplary particular, L-Dopamide is reacted with one or two equivalents of alkylhalide (e.g., methyl bromide), to thereby produce a compound according to the present invention where $R_1$ and/or $R_2$ are alkyl. Alternatively, this compound can be prepared by reacting L-DOPA methyl ester with a mono- or dialkyl ammonium salt.

In yet another exemplary particular, L-DOPA methyl ester is reacted with an acyl chloride of a fatty acid, to thereby produce a compound according to the present invention, where $R_1$ and/or $R_2$ are fatty acid acyl.

In cases where $R_8$ and $R_9$ in the formula above are each independently selected from the group consisting of alkyl having 1-30 carbon atoms, alkenyl having 1-30 carbon atoms, alkynyl having 1-30 carbon atoms, cycloalkyl, halo, aryl, O-carboxy, C-carboxy, carbonyl, thiocarbonyl, O-carbamyl, O-thiocarbamyl, and a fatty acid acyl, or, alternatively, $R_8$ and $R_9$ form a five- or six-membered ring, and $R_{10}$ and $R_{11}$ are each hydrogen, the process is effected by reacting L-DOPA with a reactive derivative of the alkyl having 1-30 carbon atoms, alkenyl having 1-30 carbon atoms, alkynyl having 1-30 carbon atoms, cycloalkyl, halo, aryl, O-carboxy, C-carboxy, carbonyl, thiocarbonyl, O-carbamyl, O-thiocarbamyl, and/or the fatty acid corresponding to the above, and thereafter reacting the resulting product with ammonia or else, as is described hereinabove.

Hence, in one exemplary particular, L-DOPA is reacted with an alkyl halide, to thereby produce an alkylamine L-DOPA derivative as the starting material in the process described hereinabove.

In another exemplary particular, L-DOPA is reacted with a carboxylic anhydride (e.g., a mixture of acetic acid and acetic anhydride), to thereby produce a N-carbonyl L-DOPA derivative (e.g., N-acetyl L-DOPA).

In yet another exemplary particular, L-DOPA is reacted with a fatty acid acyl chloride, to thereby produce a N-fatty acid acyl L-DOPA derivative.

The above L-DOPA derivatives can be then reacted as described above, to yield the corresponding mono- or di-amide derivative.

In a preferred embodiment, the products obtained as described above are thereafter purified. The purification is preferably effected by re-crystallization (e.g., lyophilization). Further preferably, the purification is effected by means of column chromatography (e.g., silica-gel chromatography), prior to and/or after the re-crystallization.

The compounds prepared according to the process of the present invention preferably has a purity of more than 90%, more preferably of more than 93% and more preferably of more than 97%.

In another preferred embodiment, the re-crystallization step is performed in the presence of one or more antioxidant(s), such that the final product includes a mixture of the compound of the present invention and the antioxidant(s). The addition of the antioxidant provides for improved stability and particularly in vivo stability of the compounds, and further provides for neuroprotection against oxidative stress, which is typically associated with L-DOPA treatment, and with the biosynthesis and degradation of dopamine and other catecholamines.

Representative examples of antioxidants that are usable in this context of the present invention include, without limitation, ascorbic acid, sodium metabisulfate, lipoic acid, N-acetyl cysteine, CB4 (N-acetyl CysGlyProCys amide), CB3 (N-acetyl CysProCys amide), AD4 (N-acetyl cysteine amide), AD6 (N-acetylGluCysGly amide), AD7 (N-acetyl-CysGly amide) and Vitamin E.

Any of the L-DOPA amide derivatives described hereinabove can be formulated into a pharmaceutical composition, which can be efficiently used in the treatment of various conditions associated with impaired dopaminergic signaling.

As used herein, the phrase "dopaminergic signaling" describes signaling pathways, typically neuronal signaling pathways, which are associated with dopamine input. The phrase "a condition associated with impaired dopaminergic signaling" according to the present invention therefore includes a condition that involves one or more impaired signaling pathways as described above, and therefore typically involves a reduced level or activity of dopamine.

The compounds of the present invention can serve as novel L-DOPA prodrugs, whereas L-DOPA acts as a prodrug of dopamine. Administration of the compounds of the present invention therefore provides for elevated dopamine levels in patients suffering from impaired dopaminergic signaling.

Hence, according to another aspect of the present invention there is provided a pharmaceutical composition, which comprises the compounds of the present invention, described hereinabove, and a pharmaceutically acceptable carrier.

The pharmaceutical composition of the present invention can be used in the treatment of Parkinson disease, as well as other dopaminergic signaling related conditions such as, but not limited to, Tourette's syndrome, attention deficit hyperactive disorder, generation of pituitary tumors and schizophrenia.

As used herein a "pharmaceutical composition" refers to a preparation of one or more of the compounds described herein, with other chemical components such as pharmaceutically suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

In one embodiment of the present invention, the carrier is an aqueous solution. Preferably the aqueous solution is a buffered acidic aqueous solution, which can include, for example, hydrochloric acid, sulfuric acid, tartaric acid, phosphoric acid, citric acid, fumaric acid, acetic acid, ascorbic acid and the like. In such an aqueous buffered solution, the L-DOPA amide derivative is in a form of a free base, and can therefore more easily penetrate through the BBB, as is discussed hereinabove.

Alternatively, the carrier can be a non-aqueous solution or a solid carrier. The latter is advantageous for, for example, oral administration, as is detailed hereinbelow.

The pharmaceutical acceptable carrier according to the present invention can further comprise one or more of the following additional ingredients.

In one example, the carrier comprises one or more antioxidants, such as, for example, ascorbic acid, vitamin E, lipoic acid, N-acetyl cysteine, CB4, CB3, AD4 AD6, AD7 or any other pharmaceutically acceptable antioxidants.

In another example, the carrier comprises a decarboxylase inhibitor, which is aimed at inhibiting an undesired enzymatic decarboxylation of DOPA to dopamine in the periphery. Any decarboxylase inhibitor can be added to the pharmaceutical composition of the present invention, with DOPA decarboxylase inhibitors such as carbidopa or benserazide, or monoamine oxidase-B (MAO B) inhibitors such as deprenyl, being preferred.

Techniques for formulation and administration of drugs may be found in "Remington's Pharmaceutical Sciences," Mack Publishing Co., Easton, Pa., latest edition.

Routes of administration: The pharmaceutical composition of the present invention can be formulated for various routes of administration. Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections.

Composition/formulation: Pharmaceutical compositions of the present invention may be manufactured by processes well known in the art, e.g., by means of conventional mixing, dissolving, granulating, dragee-making, levigating, emulsifing, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

In addition to the formulations described previously, a compound of the present invention may also be formulated for local administration, such as a depot preparation. Such long acting formulations may be administered by implantation (for example subcutaneously or intramuscularly) or by intramuscular injection. Thus, for example, the compound may be formulated with suitable polymeric or hydrophobic materials (for example, as an emulsion in an acceptable oil) or ion exchange resins, or as sparingly soluble derivatives such as sparingly soluble salts.

Formulations for topical administration may include, but are not limited to, lotions, suspensions, ointments gels, creams, drops, liquids, sprays emulsions and powders.

According to a preferred embodiment of the present invention, the pharmaceutical composition is designed for a slow release of the compound. The composition includes particles including a slow release carrier (typically, a polymeric carrier), and the compound. Slow release biodegradable carriers are well known in the art. These are materials that may form particles that may capture therein an active compound(s) and slowly degrade/dissolve under a suitable environment (e.g., aqueous, acidic, basic, etc.) and thereby degrade/dissolve in body fluids and release the active compound(s) therein. The particles are preferably nanoparticles (i.e., in the nanometer range, e.g., in the range of about 1 to about 500 nm in diameter, preferably about 50-200 nm in diameter, most preferably about 100 nm in diameter).

The pharmaceutical compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include Parkinson disease and related conditions associated with impaired dopaminergic signaling, as described hereinabove.

Hence, according to a preferred embodiment of the present invention, the pharmaceutical composition described hereinabove is packaged in a packaging material and identified in print, in or on the packaging material for use in the treatment of a condition associated with impaired dopaminergic signaling, as is described hereinabove.

According to another aspect of the present invention, each of the compounds of the present invention described above can be used for the manufacture of a medicament identified for the treatment of a condition associated with impaired dopaminergic signaling. Manufacturing the medicament can be effected as detailed hereinabove.

According to yet another aspect of the present invention there is provided a method of treating a condition associated with impaired dopaminergic signaling, as described hereinabove. The method is effected by administering to a subject in need thereof a therapeutically effective amount of any of the compounds described herein, either per se, or, more preferably, as a part of the pharmaceutical composition described hereinabove.

Hence, the method, according to this aspect of the present invention, can further be effected by co-administering to the subject, one or more antioxidants, as is detailed hereinabove, and/or an inhibitory effective amount of one or more decarboxylase inhibitors, as described hereinabove.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "administering" as used herein refers to a method for bringing a compound of the present invention and an affected area in the brain together in such a manner that the compound can affect the affected area.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this method of the invention, a therapeutically effective amount, also referred to herein as a therapeutically effective dose, can be estimated initially from cell culture assays. Such information can be used to more accurately determine useful doses in humans. Initial dosages can also be estimated from in vivo data. Using these initial guidelines one having ordinary skill in the art could determine an effective dosage in humans.

Moreover, toxicity and therapeutic efficacy of the compounds described herein can be determined by standard pharmaceutical procedures in cell cultures or experimental animals. Compounds which exhibit high therapeutic indices are preferred. The data obtained from these cell cultures assays and animal studies can be used in formulating a dosage range that is not toxic for use in human. The exact formulation, route of administration and dosage can be chosen by the individual physician in view of the patient's condition. (See, e.g., Fingl et al., 1975, In: The Pharmacological Basis of Therapeutics, chapter 1, page 1).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Chemical Syntheses

Materials and Methods:

Chemicals were purchased from various chemical suppliers and were used as supplied.

Lyophilization was performed using standard technique and apparatus.

Mass spectrometry was performed as a service by IMI institute for Research and Development.

$^1$H-NMR spectra were recorded as a service by IMI institute for Research and Development.

HPLC analyses were performed on a silica reverse phase C-18 column using a gradient acetonitrile/water mixture as a mobile phase.

Chemical Syntheses:

Synthesis of L-Dopamide (LDA):

L-DOPA (10 mmol) was added in portions to a cooled solution (6° C.) of thionyl chloride (20-30 ml) in methanol. The mixture was heated to 40° C., for 24 hours, and the solvents were thereafter removed under reduced pressure. The obtained crude ester was mixed with diluted aqueous ammonia, to thereby form the amide, and the water, excess ammonia and methanol were thereafter removed under reduced pressure. The obtained residue was purified by repeated silica gel chromatography, until the fractions containing the amide product were colorless and containing more than 90% amide, as determined by HPLC (see, FIG. 1). The product was then lyophilized, the residue was re-suspended in water and was thereafter re-lyophilized, to give about 2 grams (80% yield) of the final product.

Optionally, an antioxidant is added to the product during the final stages of the lyophilization.

Purification of L-Dopamide:

The lyophilized product obtained above was purified by silica gel chromatography and an UV detection.

The purity of the final product, as determined by HPLC, was 93% (see, FIG. 1). Table 1 below presents the HPLC analysis of the purified product (L-Dopamide retention time=7.762 minutes).

TABLE 1

| Ret Time (min) | Width (min) | Area (mAU*s) | height (mAU) | Area (%) |
|---|---|---|---|---|
| 6.247 | 0.1133 | 10.50535 | 1.48864 | 0.5394 |
| 6.4279 | 0.0950 | 140.12785 | 21.22509 | 4.7938 |
| 6.953 | 0.0978 | 5.70238 | 9.66882e-1 | 0.1951 |
| 7.762 | 0.3663 | 2729.70215 | 98.81075 | 93.3837 |
| 9.150 | 0.1605 | 37.06638 | 3.36604 | 1.2680 |
| Totals | | 2923.10411 | 125.85740 | |

Figure 2A:
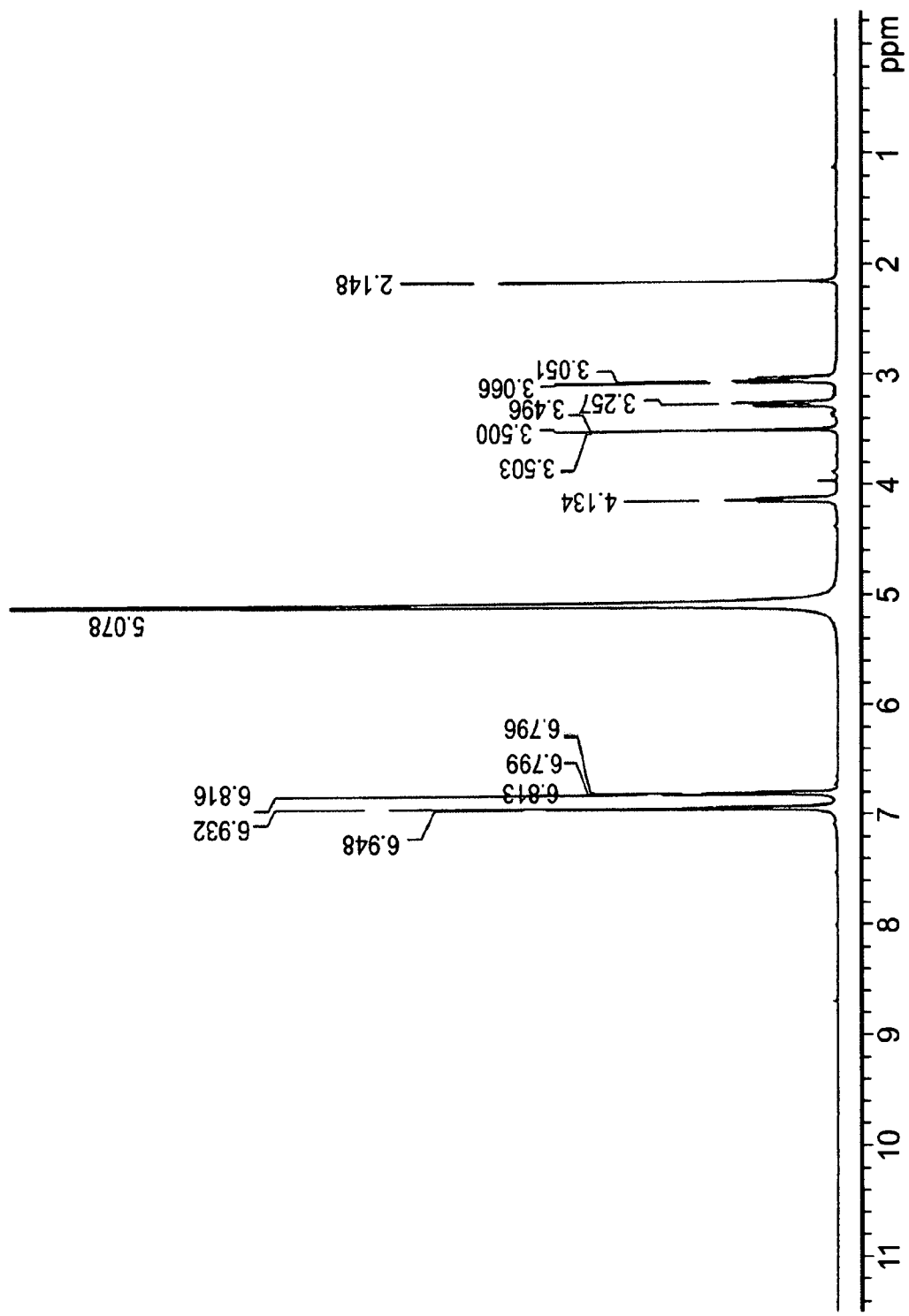
FIGS. 2a-b present and $^1$H-NMR spectrum of a representative example of a L-DOPA amide derivative (L-Dopamide) according to the present embodiments (FIG. 2a) and amplification of the aromatic zone thereof (FIG. 2b)
Figure 2B:
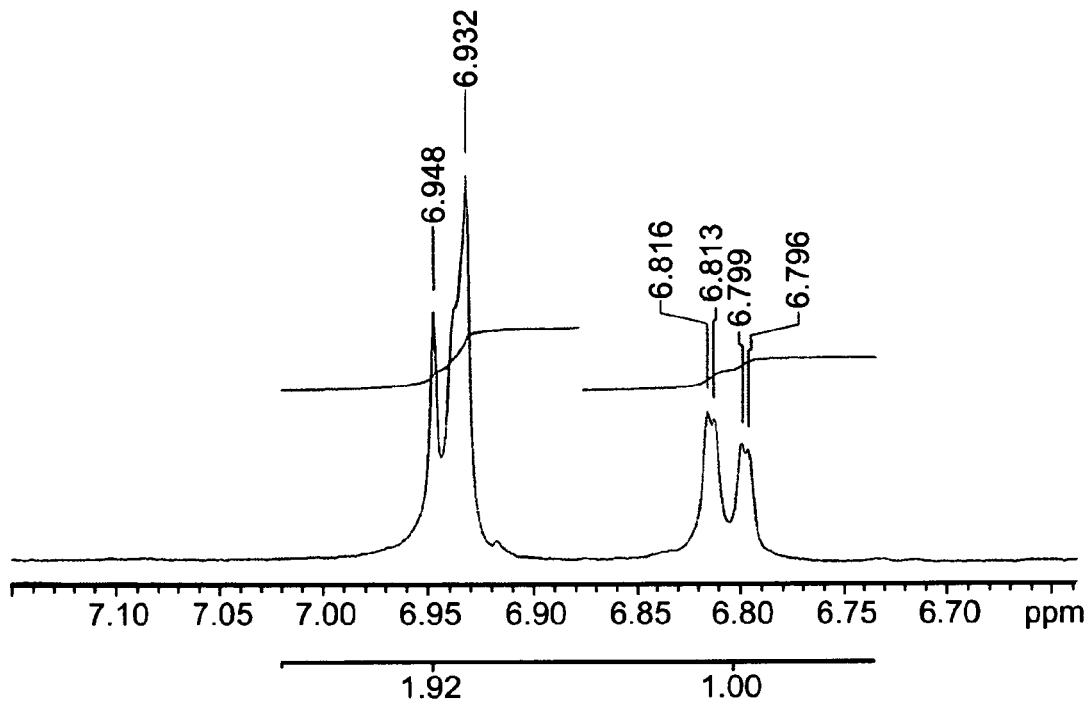

The purity of the product was further determined by $^1$H-NMR measurements. FIGS. 2a-b present the $^1$H-NMR spectrum of the final product (FIG. 2a) with amplification of the aromatic zone (FIG. 2b).

Figure 3:
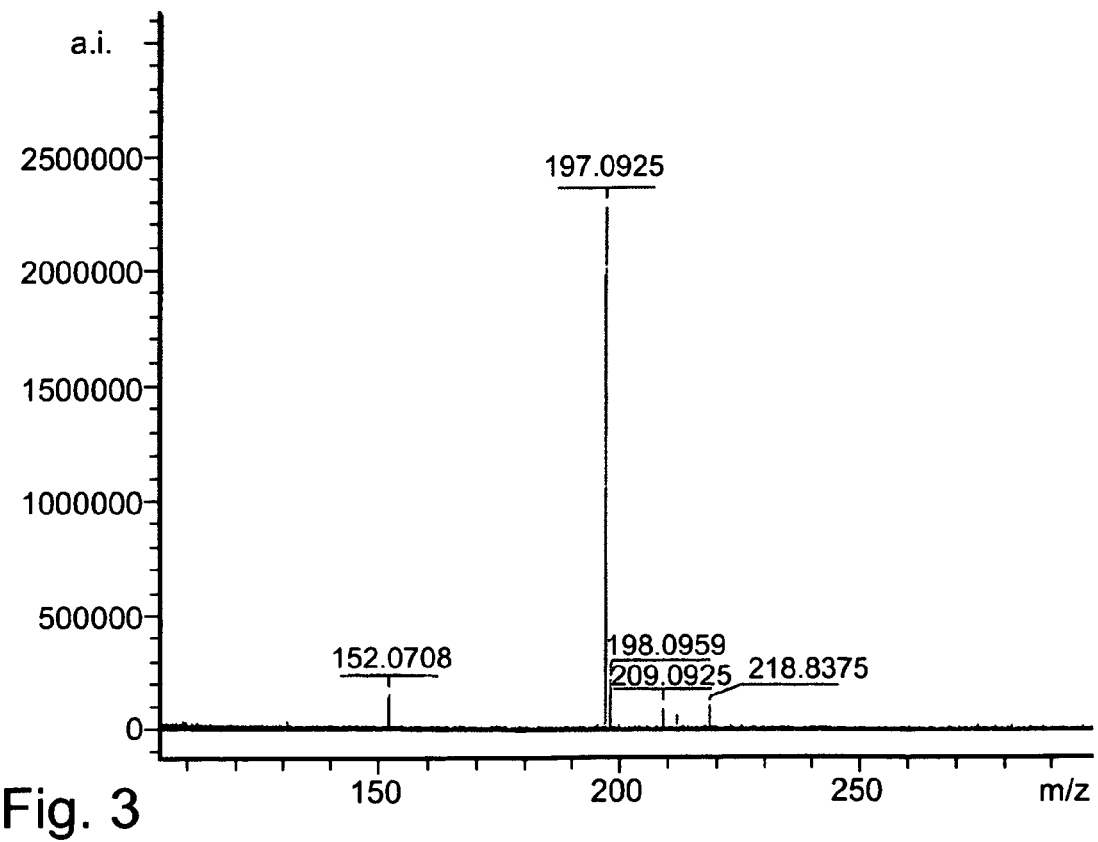
FIG. 3 presents a MS spectrum of a representative example of a L-DOPA amide derivative (L-Dopamide) according to the present embodiments.

The purity of the product was further determined by mass spectrometry, as is shown in FIG. 3.

MS (m/z): 197.0925 [M+H].

Synthesis of
α-N-acetyl-3,4-dihydroxy-benzenepropanamide
(NALDA)

L-DOPA (10 mmol) was dissolved in water and a mixture of acetic acid (20 ml) and acetic anhydride (20 ml) was added thereto. The resulting mixture was cooled to 4° C., for 2 hours and was thereafter allowed to stand for 24 hours at room temperature. Upon addition of ether (400 ml) the formed N-acetyl DOPA was precipitated. The precipitate was filtered and was thereafter added in portions to a cooled solution (6° C.) of thionyl chloride (20 ml) in methanol (20 ml). The resulting mixture was heated to 40° C. for 24 hours and thereafter the solvents were removed under reduced pressure. The obtained crude residue was reacted with aqueous ammonia, and the product was purified by repeated silica gel chromatography as described hereinabove. The product was then lyophilized, the residue was re-suspended in water twice and was thereafter lyophilized again, to give the final product.

Optionally, an antioxidant is added to the product during the final stages of lyophilization.

Activity Assays

In Vivo Studies:

The in vivo activity of LDA administered intravenously (iv) and intraperitoneally (ip) was evaluated using rotations experiments, conducted and based in accordance with published studies, as follows:

Studies have shown that administration of L-DOPA together with carbidopa (alpha-methyldopa hydrazine, a peripheral dopadecarboxylase inhibitor) to rats having unilateral 6-hydroxydopamine-induced lesions of their substantia nigra, resulted in increased concentration of striatal dopamine and its metabolites [Karoum et al, (1988) D-dopa and L-dopa similarly elevate brain dopamine and produce turning behavior in rats. Brain Res. 440(1):190-4].

As mentioned hereinabove, Parkinson's disease (PD) is thought to be caused by a breakdown in dopamine mediated communication between the substantia nigra and the striatum which controls movement, balance, and walking. Patients with Parkinson's disease are missing about 80% of the cells in the substantia nigra, and there is a corresponding loss of about 80% of dopamine in the striatum.

One method of measuring the effectiveness of a PD drug is to monitor motor behavior of PD induced laboratory animals, which follows the seminal work of S. B. Dunnet and co-workers [Bjorklund, A. et al., 1982, Nature 298(5875): 652-4]. Briefly, Dunnet's experiment uses PD induced animal models which are treated with a unilateral lesion to the brain that effects their motorial behavior. In case of rats, they turn away from the side of the lesion when treated with an agent which increases the dopamine brain level. In order to quantify this effect, a device called rotometer is used, which records the circling behavior of the tested rat by counting the number of clockwise (CW) and counter clockwise (CCW) rotations the animal is turning in a hemisphere-shaped bowl which encourages a circling behavior. Rats with induced PD will exhibit a marked turning asymmetry, and an effective PD drug will correct that effect and cause the rats to circle in a more balanced CW versus CCW manner.

Thus, twenty unilaterally 2,4,5-trihydroxyphenethylamine (6-hydroxydopamine)-lesioned male rats, weighing about 300 grams (obtained from Harlan, Rehovoth Israel) were treated with LDA and carbidopa, as is detailed hereinbelow. The rotations induced were monitored similar to the protocol used for L-DOPA and carbidopa in studies conducted by Gilgun-Sherki et al. (2003) [The CB1 cannabinoid receptor agonist, HU-210, reduces levodopa-induced rotations in 6-hydroxydopamine-lesioned rats. Pharmacol Toxicol. 93(2):66-70].

Treatment was performed by intravenously or intraperitoneally administering the LDA.

Intravenous (iv) Experiments: Rats were intravenously injected with 24 mg/kg or 40 mg/kg LDA. All rats received 4 mg/kg carbidopa, intraperitoneally, 15 minutes before LDA administration. Table 2 below summarizes the preliminary results obtained.

TABLE 2

| Rat No. | Treatment | CW | CCW | CW − CCW |
|---|---|---|---|---|
| 1 | LDA + Carbidopa 40:4 | 1563 | 724 | 839 |
| 2 | LDA + Carbidopa 40:4 | 970 | 14 | 956 |
| 3 | LDA + Carbidopa 40:4 | 573 | 59 | 514 |
| 4 | LDA + Carbi DOPA 24:4 | 686 | 128 | 558 |
| 5 | LDA + Carbi DOPA 24:4 | 629 | 134 | 495 |

As demonstrated in Table 2, the results clearly indicate that intravenous administration of LDA, together with carbidopa, is similar in its magnitude and duration to L-DOPA (see, Gilgun-Sherki et al., cited supra). This effect lasts for more than 2 hours (data not shown). The difference between the rotations seems to be more correlated with the specific lesion of the rat, than with the treatment.

These results further indicate that the co-administration of carbidopa positively affect the activity of LDA, as can be seen by the positive effect of increasing the relative amount of carbidopa with respect to the amount of LDA.

Intraperitoneal Experiments: Four rats were treated with 6-hydroxydopamine (8 μg/rat). Rats were then administered with carbidopa (4 mg/kg i.p), and 15 minutes thereafter with 15 mg/kg LDA, administered intraperitoneally. Immediately after LDA injection the rotometer was activated and the rats were monitored during 3 hours.

Table 3 below summarizes the preliminary results obtained.

TABLE 3

| Rat No. | Treatment | Weight (mg) | CW | CCW | CW − CCW |
|---|---|---|---|---|---|
| 1 | LDA + carbidopa | 300 | 56 | 22 | 34 |
| 2 | LDA + carbidopa | 364 | 361 | 50 | 311 |
| 3 | LDA + carbidopa | 340 | 123 | 74 | 49 |
| 4 | LDA + carbidopa | 394 | 111 | 109 | 2 |

These results further indicate that LDA, administered intraperitoneally, in highly active in improving the behavior of lesioned animals.

In Vitro Studies:

DOPA-decarboxylase assay: As discussed hereinabove, one of the limitations associated with treatment with L-DOPA is its decarboxylation in the periphery by a DOPA decarboxylase, which reduces the amount the amount of L-DOPA that crosses the BBB. Hence, the ability of LDA to serve as a substrate of a DOPA decarboxylase was tested and compared to that of DOPA ethyl ester (compound I).

The assay was carried out according to Hadjiconstantinou et al. [Aromatic L-amino acid decarboxylase activity of mouse striatum is modulated via dopamine receptors. J Neurochem. 1993 June; 60(6):2175-80], using the mouse striatum as a source of the decarboxylase enzyme.

The activity of the DOPA decarboxylase was thus tested with L-DOPA, DOPA-ethyl ester and LDA. L-DOPA ethyl ester (Compound 1), known as a much poorer substrate of the decarboxylase, served as a control was used as a control in these assays.

Figure 4:
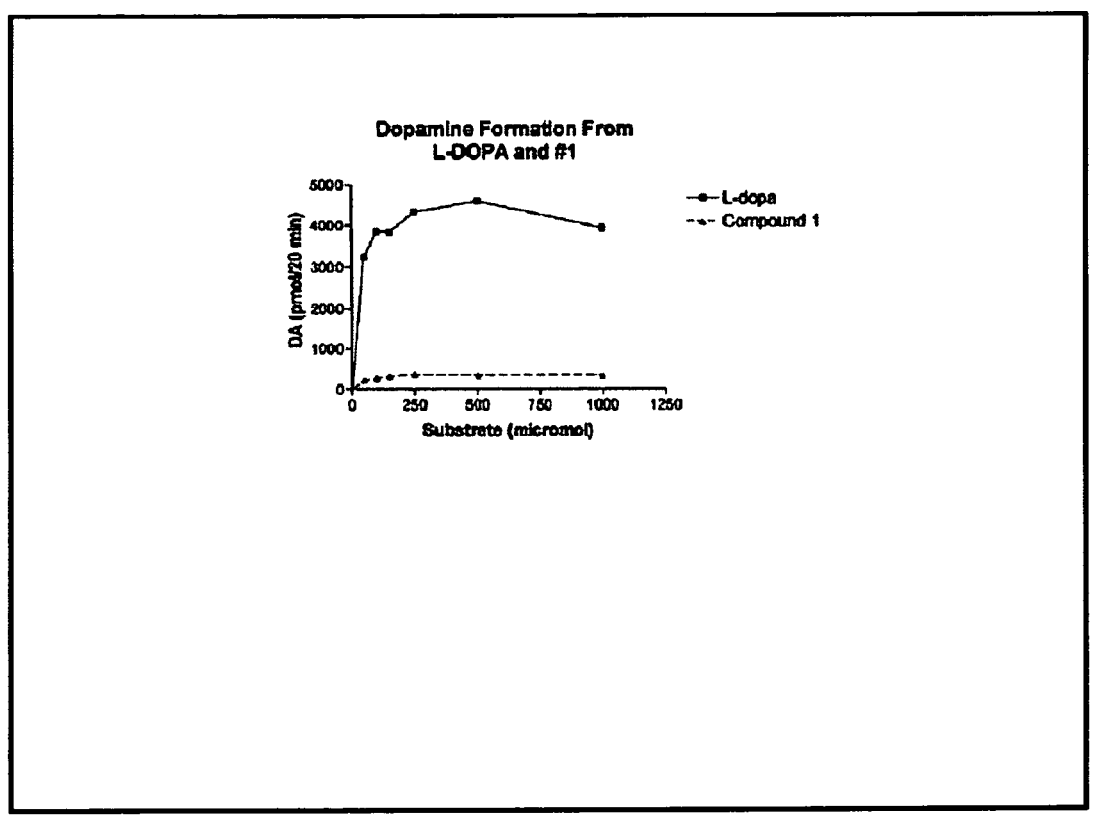
FIG. 4 presents comparative plots demonstrating the activity of a DOPA decarboxylase with L-DOPA and L-DOPA ethyl ester (Compound 1) as substrates.

Table 4 below and FIG. 4 presents the results obtained with L-DOPA and L-DOPA-ethyl ester and clearly show that indeed L-DOPA-ethyl ester is a poor substrate of the decarboxylase, as compared with L-DOPA.

No activity of the enzyme was detected with LDA. The assay was performed twice and there no formation of dopamine was observed under the assay conditions. These results thus clearly indicate that LDA is not a substrate of DOPA-decarboxylase.

TABLE 4

| Substrate (micromoles) | L-DOPA | Compound 1 |
|---|---|---|
| 50 | 3241 | 227 |
| 100 | 3839 | 278 |
| 150 | 3828 | 328 |
| 250 | 4332 | 371 |
| 500 | 4612 | 357 |
| 1000 | 3933 | 350 |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A compound of the general formula:

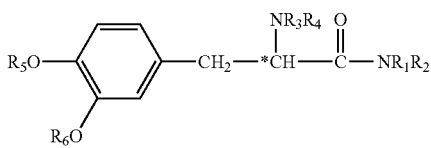

wherein:
*C denotes a chiral carbon with an S-configuration;
R₁ and R₂ are each independently selected from the group consisting of hydrogen, alkyl having 1-30 carbon atoms, alkenyl having 1-30 carbon atoms, alkynyl having 1-30 carbon atoms, cycloalkyl, aryl, O-carboxy, C-carboxy, carbonyl, thiocarbonyl, O-carbamyl, O-thiocarbamyl and a fatty acid acyl,
R₃ and R₄ are each independently selected from the group consisting of hydrogen, alkyl having 1-30 carbon atoms, alkenyl having 1-30 carbon atoms, alkynyl having 1-30 carbon atoms, cycloalkyl, aryl, O-carboxy, C-carboxy, thiocarbonyl, O-carbamyl, O-thiocarbamyl and a fatty acid acyl,
or, alternatively, R₁ and R₂ and/or R₃ and R₄ form a five- or six-membered ring; and
R₅ and R₆ are each independently selected from the group consisting of hydrogen, cycloalkyl, aryl and phosphonyl,
or a pharmaceutically acceptable salt thereof,
with the proviso that when R₃ and R₄ are both hydrogen, R₁ and/or R₂ are not hydrogen, methyl or alkyl, and R₅ and/or R₆ are not hydrogen,
the compound being characterized by high permeability through the blood brain barrier.

2. A compound of the general formula:

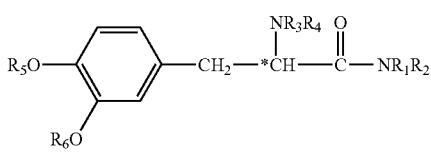

wherein:
*C denotes a chiral carbon with an S-configuration;
R₁ and R₂ are each independently selected from the group consisting of hydrogen, alkyl having 1-30 carbon atoms, alkenyl having 1-30 carbon atoms, alkynyl having 1-30 carbon atoms, cycloalkyl, aryl, O-carboxy, C-carboxy, carbonyl, thiocarbonyl, O-carbamyl, O-thiocarbamyl and a fatty acid acyl, wherein at least one of R₁ and R₂ is carbonyl,
R₃ and R₄ are each independently selected from the group consisting of hydrogen, alkyl having 1-30 carbon atoms, alkenyl having 1-30 carbon atoms, alkynyl having 1-30 carbon atoms, cycloalkyl, aryl, O-carboxy, C-carboxy, thiocarbonyl, O-carbamyl, O-thiocarbamyl and a fatty acid acyl,
or, alternatively, R₃ and R₄ form a five- or six-membered ring; and
R₅ and R₆ are each independently selected from the group consisting of hydrogen, cycloalkyl, aryl and phosphonyl,
or a pharmaceutically acceptable salt thereof,
with the proviso that when R₃ and R₄ are both hydrogen, R₁ and/or R₂ are not hydrogen, methyl or alkyl, and R₅ and/or R₆ are not hydrogen.

3. A compound of the general formula:

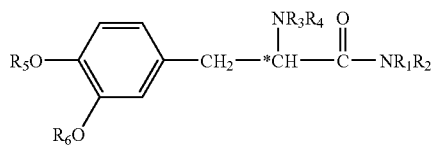

wherein:
*C denotes a chiral carbon with an S-configuration;
R₁ and R₂ are each independently selected from the group consisting of hydrogen, alkyl having 1-30 carbon atoms, alkenyl having 1-30 carbon atoms, alkynyl having 1-30 carbon atoms, cycloalkyl, aryl, O-carboxy, C-carboxy, carbonyl, thiocarbonyl, O-carbamyl, O-thiocarbamyl and a fatty acid acyl,
R₃ and R₄ are each independently selected from the group consisting of hydrogen, alkyl having 1-30 carbon atoms, alkenyl having 1-30 carbon atoms, alkynyl having 1-30 carbon atoms, cycloalkyl, aryl, O-carboxy, C-carboxy, thiocarbonyl, O-carbamyl, O-thiocarbamyl and a fatty acid acyl,
or, alternatively, R₁ and R₂ and/or R₃ and R₄ form a five- or six-membered ring; and
R₅ and R₆ are each independently selected from the group consisting of hydrogen, cycloalkyl, aryl and phosphonyl,
or a pharmaceutically acceptable salt thereof,
with the proviso that:
when R₃ and R₄ are both hydrogen, R₁ and/or R₂ are not hydrogen, methyl or alkyl, and R₅ and/or R₆ are not hydrogen; and
at least one of R₁, R₂, R₃ and R₄ is selected from the group consisting of an alkyl having 1-30 carbon atoms, an alkenyl having 1-30 carbon atoms and an alkynyl having 1-30 carbon atoms.

4. A compound of the general formula:

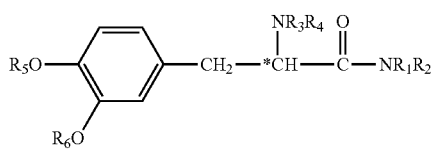

wherein:
*C denotes a chiral carbon;
R₁, R₂, R₃ and R₄ are each independently selected from the group consisting of hydrogen, alkyl having 1-30 carbon atoms, alkenyl having 1-30 carbon atoms, alkynyl having 1-30 carbon atoms, cycloalkyl, aryl, O-carboxy, C-carboxy, carbonyl, thiocarbonyl, O-carbamyl, O-thiocarbamyl and a fatty acid acyl, or, alternatively, $R_1$ and $R_2$ and/or $R_3$ and $R_4$ form a five- or six-membered ring; and $R_5$ and $R_6$ are each independently selected from the group consisting of hydrogen, alkyl, cycloalkyl, aryl and phosphonyl, or a pharmaceutically acceptable salt thereof, wherein at least one of $R_1$, $R_2$, $R_3$ and $R_4$ is a fatty acid acyl.

5. The compound of claim 4, wherein said fatty acid is selected from the group consisting of myristic acid, lauric acid, palmitic acid, stearic acid, oleic acid, arachidonic acid, linoleic acid and linolenic acid.

6. A pharmaceutical composition comprising, as an active ingredient, a compound of the general formula:

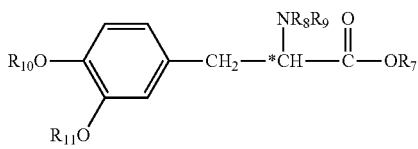

wherein:

*C denotes a chiral carbon;

$R_1$, $R_2$, $R_3$ and $R_4$ are each independently selected from the group consisting of hydrogen, alkyl having 1-30 carbon atoms, alkenyl having 1-30 carbon atoms, alkynyl having 1-30 carbon atoms, cycloalkyl, halo, aryl, O-carboxy, C-carboxy, carbonyl, thiocarbonyl, O-carbamyl, O-thiocarbamyl and a fatty acid acyl, or, alternatively, $R_1$ and $R_2$ and/or $R_3$ and $R_4$ form a five- or six-membered ring; and $R_5$ and $R_6$ are each independently selected from the group consisting of hydrogen, alkyl, cycloalkyl, aryl and phosphonyl, or a pharmaceutically acceptable salt thereof, and a pharmaceutically acceptable carrier.

7. The pharmaceutical composition of claim 6, packaged in a packaging material and identified in print, in or on said packaging material, for use in a condition selected from the group consisting of Parkinson disease, Tourette's syndrome, attention deficit hyperactive disorder, generation of pituitary tumors and schizophrenia.

8. The pharmaceutical composition of claim 6, further comprising at least one antioxidant.

9. The pharmaceutical composition of claim 8, wherein said at least one antioxidant is selected from the group consisting of ascorbic acid, sodium metabisulfate, lipoic acid, N-acetyl cysteine, CB4, CB3, AD4, AD6, AD7 and Vitamin E.

10. The pharmaceutical composition of claim 6, further comprising at least one decarboxylase inhibitor.

11. The pharmaceutical composition of claim 10, wherein said decarboxylase inhibitor is an L-DOPA decarboxylase inhibitor.

12. The pharmaceutical composition of claim 6, further comprising at least one monoamine oxidase-B inhibitor.

13. The pharmaceutical composition of claim 6, wherein said compound is selected from the group consisting of α-amino-3,4-dihydroxy-benzenepropanamide, α-N-acetyl-3,4-dihydroxy-benzenepropanamide and pharmaceutically acceptable salts thereof.

14. The pharmaceutical composition of claim 6, being formulated for oral administration.

15. The pharmaceutical composition of claim 6, being formulated for transdermal administration.

16. A pharmaceutical composition comprising, as an active ingredient, a compound of the general formula:

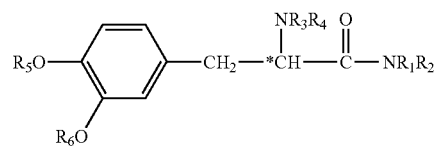

wherein:

*C denotes a chiral carbon;

$R_1$, $R_2$, $R_3$ and $R_4$ are each independently selected from the group consisting of hydrogen, alkyl having 1-30 carbon atoms, alkenyl having 1-30 carbon atoms, alkynyl having 1-30 carbon atoms, cycloalkyl, halo, aryl, O-carboxy, C-carboxy, carbonyl, thiocarbonyl, O-carbamyl, O-thiocarbamyl and a fatty acid acyl, or, alternatively, $R_1$ and $R_2$ and/or $R_3$ and $R_4$ form a five- or six-membered ring; and $R_5$ and $R_6$ are each independently selected from the group consisting of hydrogen, alkyl, cycloalkyl, aryl and phosphonyl, or a pharmaceutically acceptable salt thereof, at least one decarboxylase inhibitor, and a pharmaceutically acceptable carrier.

17. The pharmaceutical composition of claim 16, wherein said decarboxylase inhibitor is an L-DOPA decarboxylase inhibitor.

* * * * *